United States Patent [19]
Kriesel

[11] Patent Number: 6,086,560
[45] Date of Patent: Jul. 11, 2000

[54] FLUID DISPENSER WITH FILL ADAPTER

[75] Inventor: Marshall S. Kriesel, Saint Paul, Minn.

[73] Assignee: Science Incorporated, Bloomington, Minn.

[21] Appl. No.: 09/250,040

[22] Filed: Feb. 12, 1999

Related U.S. Application Data

[63] Continuation-in-part of application No. 08/729,326, Oct. 15, 1996, Pat. No. 5,873,857, which is a continuation-in-part of application No. 08/577,496, Dec. 22, 1995, Pat. No. 5,700,244, which is a continuation-in-part of application No. 08/192,031, Feb. 3, 1994, Pat. No. 5,484,415, which is a continuation-in-part of application No. 08/156,685, Nov. 22, 1993, Pat. No. 5,433,709, which is a continuation-in-part of application No. 08/053,723, Apr. 26, 1993, Pat. No. 5,354,278, which is a continuation-in-part of application No. 07/870,521, Apr. 17, 1992, Pat. No. 5,263,940.

[51] Int. Cl.[7] .................................................. A61M 37/00
[52] U.S. Cl. ............................. 604/131; 128/DIG. 12
[58] Field of Search ............................. 604/131, 132, 604/133, 151, 213, 218, 187, 190; 128/DIG. 12

[56] References Cited

U.S. PATENT DOCUMENTS

| | | |
|---|---|---|
| 3,378,008 | 4/1968 | Ogle . |
| 3,593,381 | 7/1971 | Oble . |
| 3,828,779 | 8/1974 | Ogle . |
| 4,180,070 | 12/1979 | Genese . |
| 4,259,956 | 4/1981 | Ogle . |
| 4,296,747 | 10/1981 | Ogle . |
| 4,607,671 | 8/1986 | Aalto et al. . |
| 4,886,495 | 12/1989 | Reynolds . |
| 5,067,984 | 11/1991 | Haber et al. . |
| 5,171,214 | 12/1992 | Kolber et al. . |
| 5,354,278 | 10/1994 | Kriesel ................................... 604/132 |
| 5,533,993 | 7/1996 | Maier . |
| 5,700,244 | 12/1997 | Kriesel ................................... 604/132 |
| 5,721,382 | 2/1998 | Kriesel et al. ........................ 73/706 X |
| 5,873,857 | 2/1999 | Kriesel ................................... 604/131 |

Primary Examiner—John D. Yasko
Attorney, Agent, or Firm—James E. Brunton, Esq.

[57] ABSTRACT

An elastomeric bladder stored energy type medicament delivery apparatus which can be filled with a medicinal fluid using a closed-end, vial-type fill container and after being filled, can efficiently deliver the medicinal fluid to the patient at a controlled rate. The closed-end, vial-type fill means can be readily connected to and disconnected from the novel fluid delivery component of the apparatus. The fluid delivery device can also be filled by means of a secondary reservoir fill means.

27 Claims, 9 Drawing Sheets

FLUID DISPENSER WITH FILL ADAPTER

This is a Continuation-In-Part application of U.S. application Ser. No. 08/729,326, filed Oct. 15, 1996, now U.S. Pat. No. 5,873,857 which is a Continuation-In-Part application of U.S. application Ser. No. 08/577,496 filed Dec. 22, 1995 and now issued into U.S. Pat. No. 5,700,244; which is a Continuation-In-Part of application Ser. No. 08/192,031 filed on Feb. 3, 1994 entitled Fluid Dispensing Apparatus and issued into U.S. Pat. No. 5,484,415; which is a Continuation-In-Part of U.S. application Ser. No. 08/156,685 filed on Nov. 22, 1993 and has now issued into U.S. Pat. No. 5,433,709 entitled Fluid Dispenser; which is a Continuation-In-Part of Ser. No. 08/053,723 filed Apr. 26, 1993 and has now issued into U.S. Pat. No. 5,354,278; which is a Continuation-In-Part application of Ser. No. 07/870,521 filed on Apr. 17, 1992 and now issued into U.S. Pat. No. 5,263,940.

BACKGROUND OF THE INVENTION

1. Field of the Invention

The present invention relates generally to infusion devices. More particularly, the invention concerns an elastomeric bladder type infusion apparatus which is used for controllably delivering a beneficial agent to a patient. The device uniquely includes adjustable flow rate means for adjusting the rate of fluid flow from the device toward the patient.

2. Discussion of the Prior Art

Many types of infusion pumps embodying an elastomeric balloon or bladder for delivery of a quantity of pharmaceutically active material to a patient have been suggested in the past. For example, U.S. Pat. No. 4,915,693 issued to Hessel discloses an infusion pump comprising an elastomeric bladder having at least an open end, and an elongate stress member extending concentrically within the entire length of the hollow portion of the bladder and having a fluid tight seal therewith. Both a filling port and an exit port are provided in the stress member, each in fluid communication with the interior of the bladder by way of an influent and an effluent lumen, respectively. The stress member has a diameter that is greater thin the relaxed internal diameter of the bladder, and has a length that exceeds the relaxed internal length of the hollow portion of the bladder, so that it prestresses the bladder in both the axial and radial directions when disposed therein, substantially filling the bladder in its unfilled state. The Hessel device also includes a one-way valve on the stress member which permits flow through the influent lumen only in the direction of the interior of the bladder.

Very early balloon type infusion devices are described in U.S. Pat. Nos. 3,468,308 and 3,469,578 issued to Bierman. These patents disclose a device for expelling a liquid from a bladder member at an extremely slow rate over an extended period of time.

One of the more advanced elastomeric bladder type devices ever developed is described in U.S. Pat. No. 5,354,278 issued to the present inventor. Because the present invention comprises an improvement to the devices disclosed in this latter patent, U.S. Pat. No. 5,354,278 is hereby incorporated by reference as though fully set forth herein. Another advanced elastomeric bladder type device is disclosed in U.S. Ser. No. 08/729,326 filed by the present inventor on Oct. 15, 1996. This application is also incorporated by reference as though fully set forth herein.

Disclosed in U.S. Pat. No. 5,721,382, issued to one of the present inventors, is a device having a flow indicator means similar to that embodied in the present invention. For this reason, U.S. Pat. No. 5,721,382 is incorporated by reference as though fully set forth herein.

None of the prior art devices known to applicant disclose the unique fill mean of the present invention for controllably filling the fluid reservoir of the dispensing device with which the fill means can be coupled.

SUMMARY OF THE INVENTION

It is an object of the present invention to provide an elastomeric bladder stored energy type medicament delivery apparatus which can be filled with a medicinal fluid using a closed end, vial type fill container and after being filled, can efficiently deliver the medicinal fluid to the patient at a controlled rate.

Another object of the invention is to provide an elastomeric bladder type fluid delivery or dispensing device of the aforementioned character in which the reservoir of the fluid delivery device can also be filled by means of a secondary reservoir fill means.

Another object of the invention is to provide a device of the character described in the preceding paragraphs in which the closed end, vial type fill means can be readily connected to and disconnected from the novel fluid delivery component of the apparatus.

Another object of the invention is to provide a fill assembly that is specially configured to mate only with a fluid delivery device having a specific fill adapter configuration.

It is another object of the invention to provide an apparatus of the aforementioned character which is highly reliable and easy-to-use by lay persons in a non-hospital environment.

Another object of the invention is to provide an apparatus which can be factory prefilled with a wide variety of medicinal fluids or one which can readily be filled in the field shortly prior to use using the novel reservoir fill component which can be removably interconnected to the lower surface of the base of the fluid dispenser.

Another object of the invention is to provide an apparatus as defined in the preceding paragraph in which the reservoir fill assembly is uniquely designed to accept a closed end vial component of conventional construction which is factory filled with the medicinal fluid to be delivered to the patient.

A further object of the invention is to provide an accurate and hightly reliable fluid delivery device which can be manufactured relatively inexpensively in large volume.

DESCRIPTION OF ONE FORM OF THE INVENTION

Figures 1, 3:
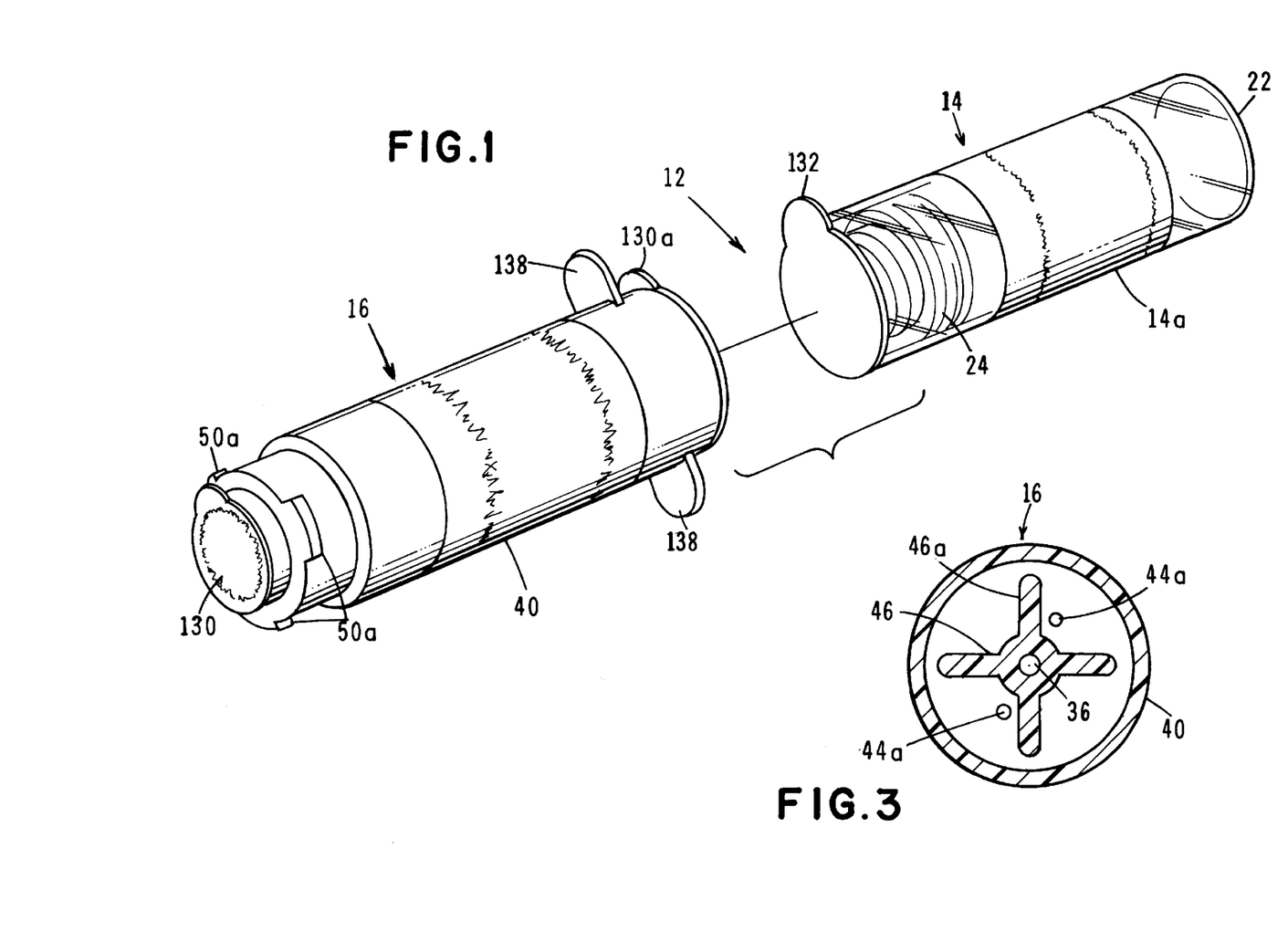
FIG. 1 is a generally perspective exploded view of one form of the fill assembly of the present invention.
FIG. 3 is a cross-sectional view taken along lines 3—3 of FIG. 2.
Figure 2:
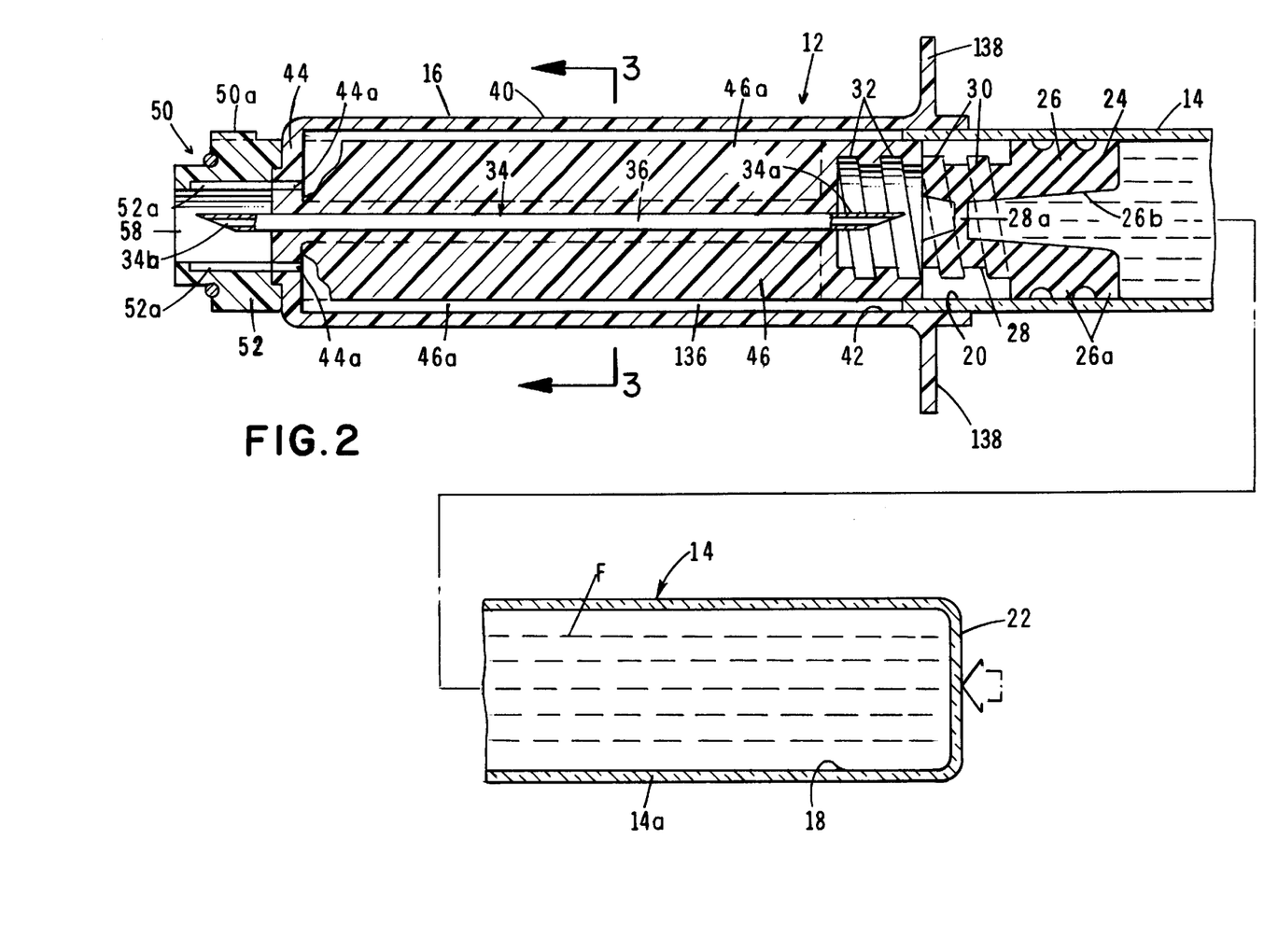
FIG. 2 is an enlarged, cross-sectional view of the fill assembly illustrated in FIG. 1 as it appears in an assembly configuration.

Referring to the drawings and particularly to FIGS. 1 through 6, one form of the fill assembly of the present invention is there illustrated and generally designated by the numeral 12 (FIG. 2). Fill assembly 12 is specially designed for use with a fluid delivery apparatus of a character presently to be described which includes a stored energy means that is changeable in configuration from a first position to a second position to act upon fluid contained within a fluid reservoir of the delivery apparatus.

Figure 4:
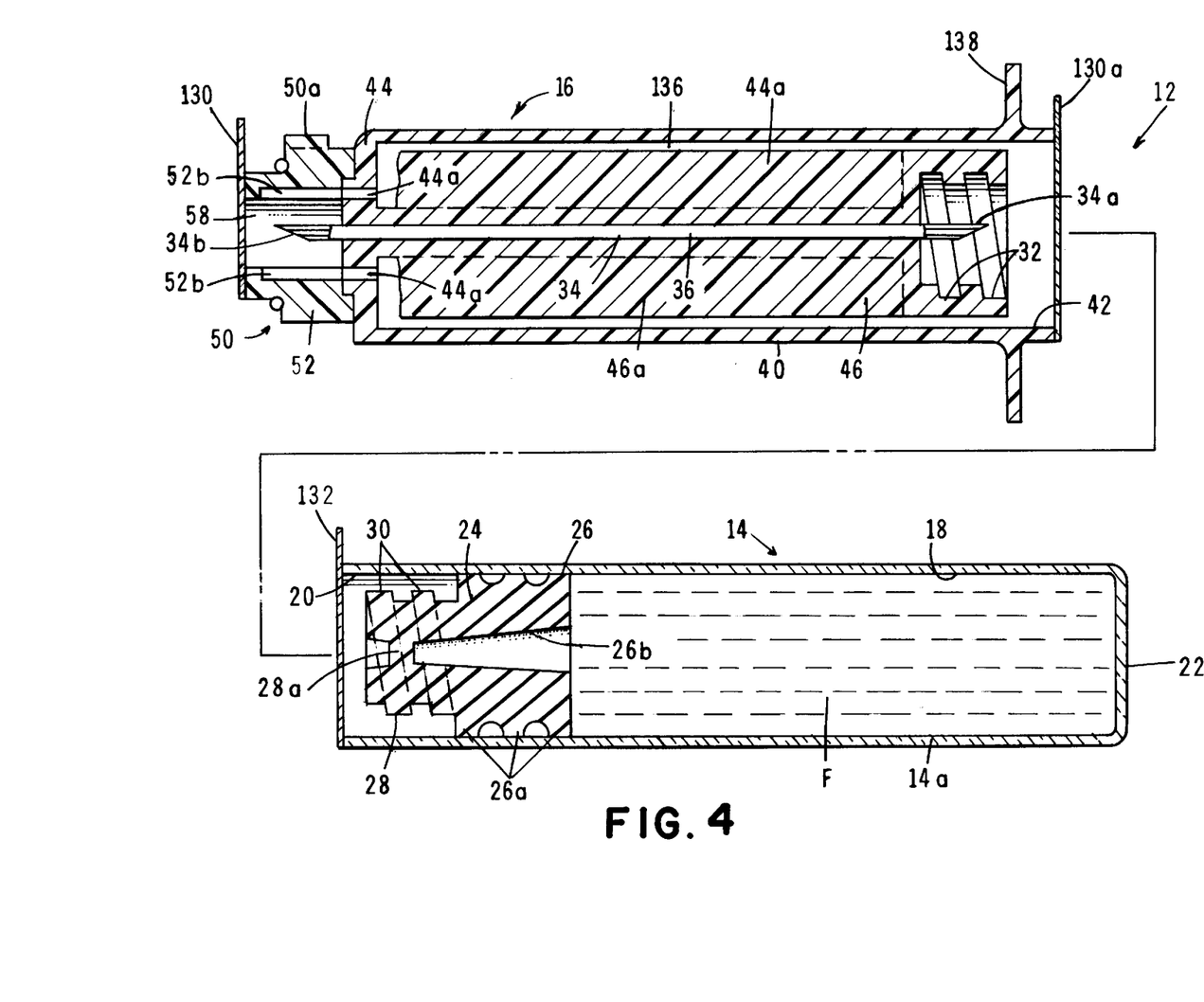
FIG. 4 is a foreshortened, exploded, cross-sectional view similar to FIG. 2, but showing the container assembly and the adapter assembly separated and ready to be operably interconnected.
Figure 5:
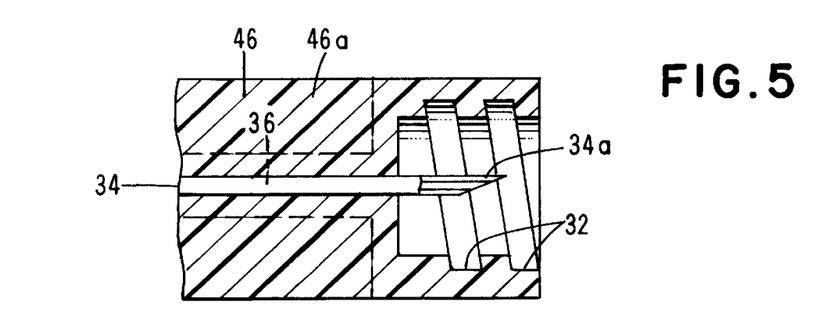
FIG. 5 is a fragmentary, cross-sectional view of the rear portion of the adapter assembly shown in FIG. 4.

As illustrated by referring to FIG. 1, the fill assembly of this form of the invention comprises a container subassembly 14 and an adapter assembly 16 which telescopically accepts the container assembly. Container subassembly 14 includes a body portion 14a, having a fluid chamber 18 for containing an injectable fluid "F" (FIG. 2). Body portion 14a is provided with a first open end 20, and a second closed end 22. First open end 20 is sealably closed by closure means here provided in the form of a plunger assembly 24 (FIG. 4). Plunger assembly 24 comprises an elastomeric plunger 26 and a connector means, or connector 28 which functions to interconnect the container assembly with the adapter assembly. Plunger assembly 24 is telescopically movable within chamber 18 of container subassembly 14 from a first location proximate first open end 20 to a second location proximate closed end 22.

As best seen in FIG. 4, connector 28 includes threads 30 which can be threadably connected to threads 32 provided on adapter assembly 16. Connector 28 also includes a pierceable central wall 28a which is pierceable by one end 34a of an elongated cannula 34 of the adapter assembly, which cannula comprises a part of the first flow control means of the adapter assembly for controlling fluid flow into a fluid flow passageway 36 formed interiorly of cannula 34. Connector 28 is integrally formed with plunger 26 in the manner shown in FIG. 4 so that as plunger 26 is moved toward closed end 22, in a manner presently to be described, connector 28 and plunger 26 will move as a unit. To prevent leakage of fluid past plunger 26, the plunger is provided with rings 26a which are of a diameter slightly greater than the inside diameter of container body 14a. Plunger 26 also includes a central fluid passageway 26b which is in open communication with chamber 18.

Referring now particularly to FIG. 4, it can be seen that adapter subassembly 16 comprises a hollow housing 40 having a first open end 42 and a second closed end 44. Container subassembly 14 is telescopically receivable within open end 42 of housing 40 in the manner shown in FIG. 2 so that the housing can be moved from the first extended position shown in FIG. 2 to a second container encapsulation position wherein container 14 is substantially encapsulated within housing 40. Provided interiorly of the adapter subassembly is a pusher means shown here as a pusher body having an elongated, generally cross shaped pusher section 46a (FIG. 3) which functions to move plunger 26 within fluid chamber 18 from the first forward position shown in FIG. 2 to the second position wherein it is disposed proximate end wall 22. Pusher body 46 also includes a head portion with a pair of passageways 44a, which permit gases trapped with the interior of the adapter body to be vented to atmosphere.

Figure 6:
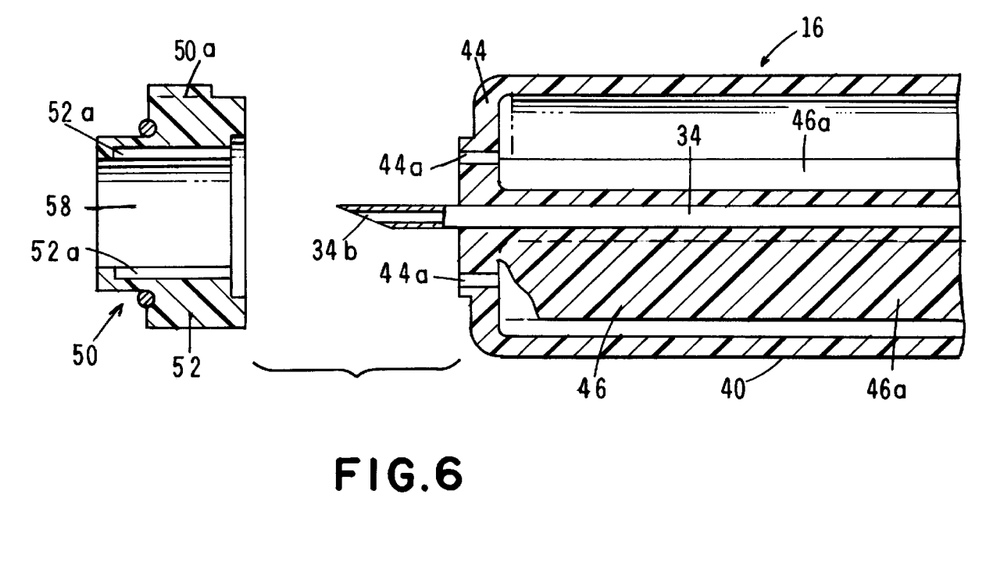
FIG. 6 is a fragmentary, cross-sectional, exploded view of the forward portion of the adapter assembly shown in FIG. 4.

Also forming a part of the adapter assembly of the invention is a cap assembly 50 (FIG. 6) which is connected to body portion 40 in the manner shown in FIG. 4. Cap assembly 50 includes a generally cylindrical exterior wall 52, the interior surface of which forms a chamber 58 into which the second end 34b of cannula 34 extends. Formed within wall 52 are vent passageways 52a which communicate with vent passageways 44a (FIG. 6). With this novel construction all gases that may be trapped with the adapter assembly can be vented to atmosphere during the reservoir filling step.

Figure 7:
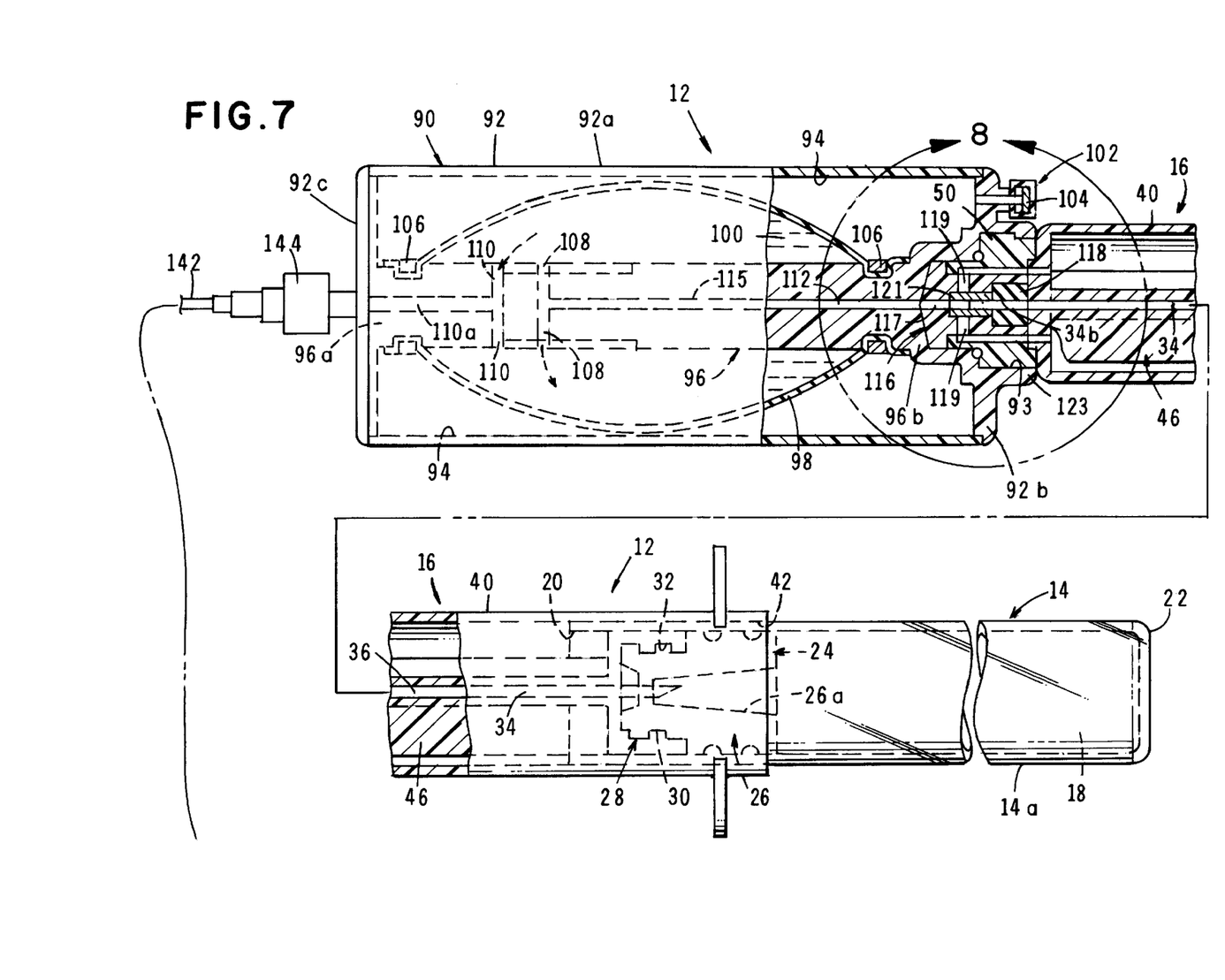
FIG. 7 is an exploded, side-elevational view of one form of fluid delivery apparatus of the invention partly broken away to show internal construction and shown with the delivery component coupled with one form of the adapter assembly of the invention.
Figure 7A:
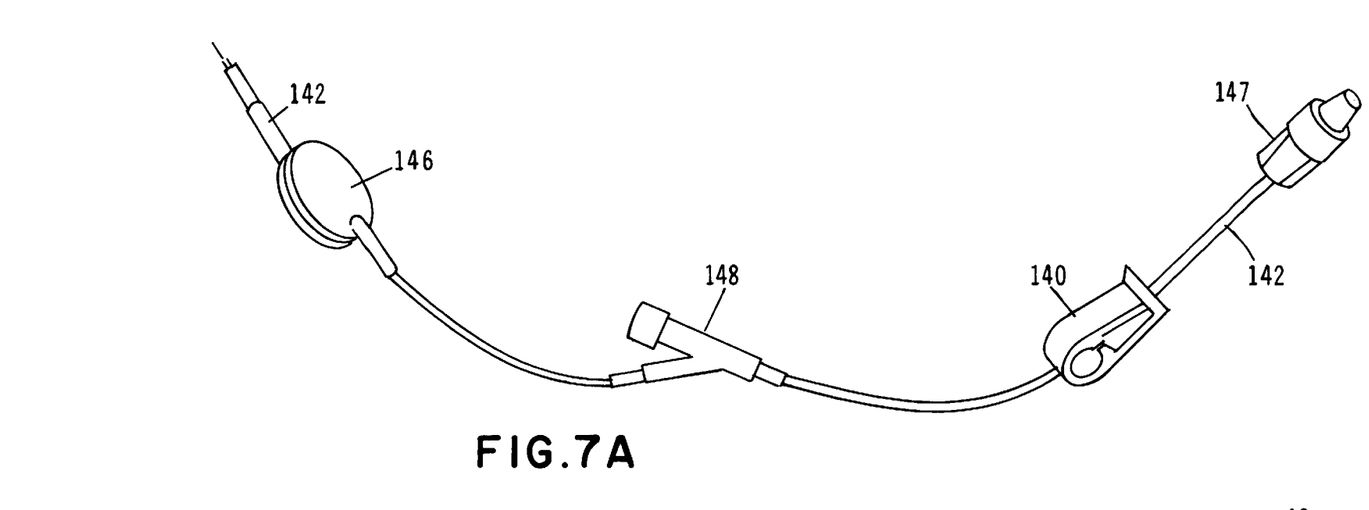

Turning next to FIGS. 7 through 11 one form of the fluid delivery assembly of the invention is there shown. As best seen in FIG. 7, the fluid delivery apparatus of this form of the invention comprises two major cooperating assemblies, namely a fluid dispensing or delivery component 90 and the previously described fill assembly 12. The fluid delivery component 90 here comprises an elongated housing 92 having an internal chamber 94, a support assembly 96 disposed within internal chamber 94, and extending longitudinally of the housing 92 and a generally cylindrically shaped, elongated elastomeric member 98. Elastomeric member 98, which forms the stored energy means of the invention, is movable from a first relaxed state to a distended state, cooperates with support assembly 96 to define a fluid reservoir 100, the outer boundary of which is defined by the distended elastomeric member 98.

Housing 92 comprises a cylindrically shaped central portion 92a and inlet and outlet end plates 92b and 92c respectively. Central section 92a and end plates 92b and 92c can be constructed of any suitable rigid plastic material such as polycarbonate and the end plates can be affixed to the central portion by any suitable means such as adhesive bonding or an appropriate sonic weldment. Plate 92b carries a first vent means for venting chamber 94 This first vent means comprises a vent assembly 102 that includes a filter element 104. Plate 92b also includes a chamber 93, which in a manner presently to be described, receives a portion of the fill assembly of this latest form of the invention. Elastomeric stored energy member 98 is securely affixed proximate its ends to support 96 by means of suitable ring clamps 106 such as self-locking plastic panduit strips.

Figures 8, 9, 10:
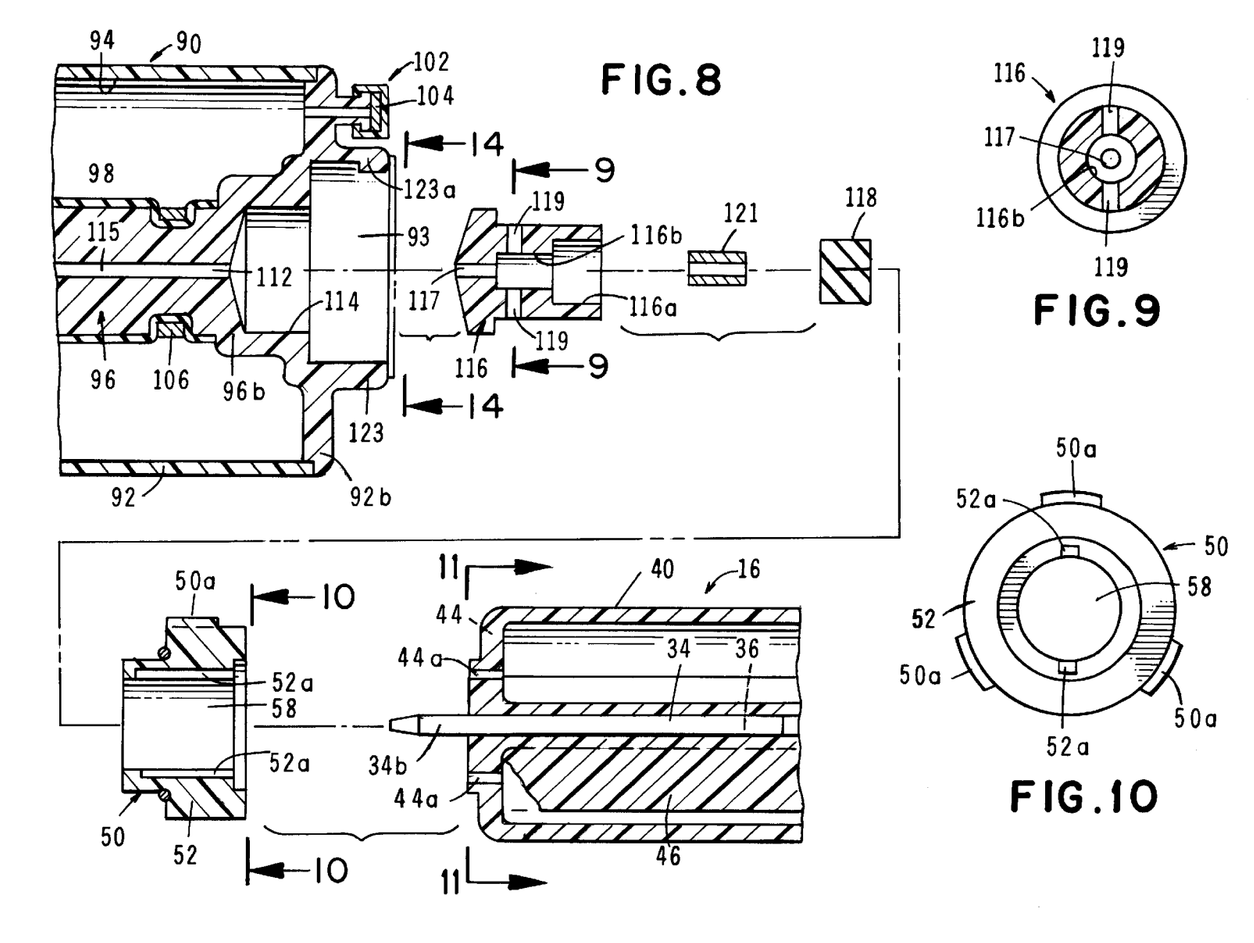
FIG. 8 is an enlarged, exploded, cross-sectional view of the portion of the apparatus of the invention designated in FIG. 8 by the area "8".
FIG. 9 is a cross-sectional view taken along lines 9—9 of FIG. 8.
FIG. 10 is an end view taken along lines 10—10 of FIG. 8.

As shown in FIG. 7, support assembly 96 has a first end portion 96a having a fluid inlet 108 and fluid outlets 110. Support assembly 96 also includes a second end portion 96b having an inlet fluid passageway 112 and an internal chamber 114 (FIG. 8). Passageway 112 is connected to inlets 108 by a longitudinally extending fluid passageway 115. Received within chamber 114 is a second vent means which is disposed within a uniquely configured insert 116 having an outlet fluid passageway 117 which communicates with passageway 115. Insert 116 is mounted within chamber 114 of end plate 92b the closure cap 50 of the adapter assembly in the manner shown in FIG. 7.

The flow control means of this form of this latest form of the invention is also mounted within insert 116 and here comprises a pierceable septum 118 that is housed within a chamber 116a formed in element 116. In a manner presently to be described, septum 118 is pierceable by end 34b of cannula 34 of adapter assembly 16. The previously mentioned second vent means uniquely functions to vent to atmosphere any gases trapped within passageway 36 of cannula 34. This second vent means here comprises a hydrophobic vent element 121 which is housed within a chamber 116b formed in element 116 (FIG. 8). Element 116 communicates with outlet passageway 119 formed in element 116 so that gases trapped within passageway 36 can flow through vent element 121 and thence to atmosphere via passageways 119. With this novel construction, the initial air purging step required during the use of conventional syringes prior to the injection step is elegantly avoided.

The dispensing component 90 of the present invention is similar in some respects to that described in U.S. Pat. No. 5,700,244. Accordingly, U.S. Pat. No. 5,700,244 is incorporated by reference as though fully set forth herein. This latter patent should be referred to for a more complete description of the details of operation, construction and materials suitable for use in forming the various components of the fluid dispenser component of the invention including elastomeric stored energy member 98.

To interconnect fill assembly 12 with fluid delivery apparatus 90, the barrel-like portion, or closure cap 50 of the adapter assembly is inserted into chamber 93 which is formed by a hub like portion 123, which portion is provided on end plate 92b. As the adapter assembly enters chamber 93, the circumferentially spaced, bayonet type connectors or locking tabs 50a of closure cap 50 (see FIGS. 8 and 10) are received between the circumferentially spaced tab receiving slots 123a formed on hub-like portion 123. Relative rotation of the fill assembly and the fluid delivery component will securely interconnect the components in the manner shown in FIG. 7. As indicated in FIG. 7, as the fill assembly 12 is mated with the delivery component 90, end 34b of cannula 34 of the adapter assembly will pierce a pierceable septum 118 which is mounted within chamber 116a of insert 116 in the manner shown in FIG. 7.

Figure 10A:
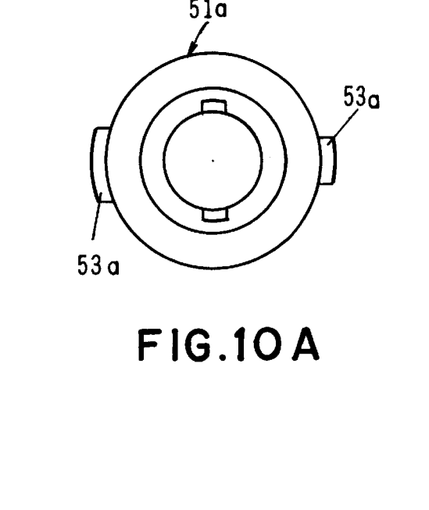
FIG. 10A is an end view of an alternate form of fill adapter having two rather than three locking tabs.
Figure 10B:
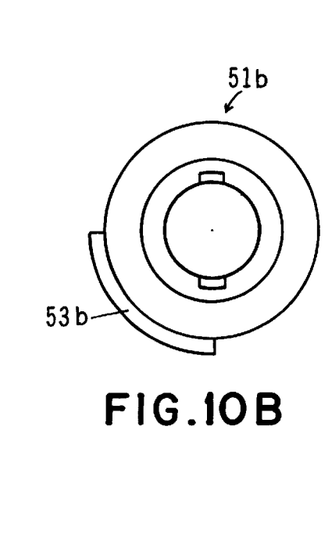
FIG. 10B is an end view of yet another form of fill adapter having but a single strategically configured locking tab.
Figure 11:
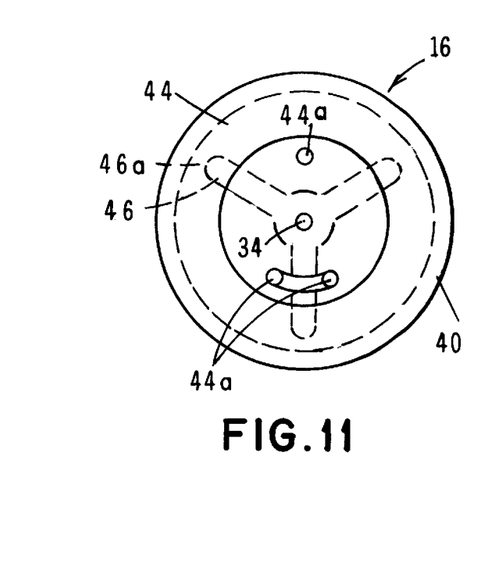
FIG. 11 is a left-end view taken along lines 11—11 of FIG. 8.

Turning to FIGS. 10A and 10B, alternate forms of the closure cap of the adapter assembly, which comprises a barrel portion of the housing of the adapter assembly, are there shown designated as 51a and 51b. Cap assembly 51a is provided with two rather than three circumferentially spaced locking tabs 53a, and cap assembly 51b is provided with a single specially configured locking tab 53b of a predetermined size and angular location.

Figure 12:
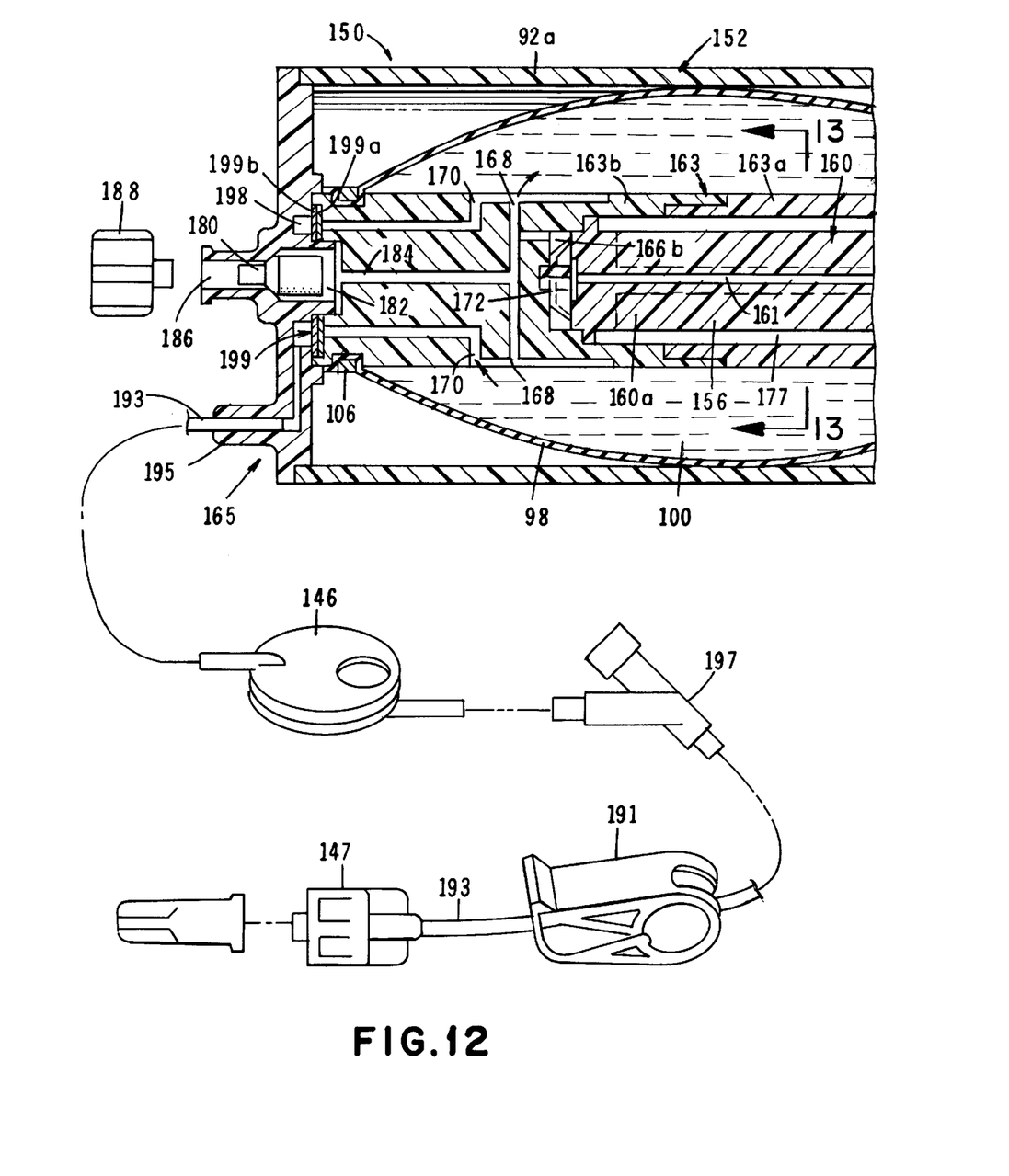
FIG. 12 is a cross-sectional, exploded view of an alternate form of the medicament dispenser of the invention showing the dispenser component operably mated with an alternate form of reservoir fill assembly.
Figures 12A, 13, 14, 14A:
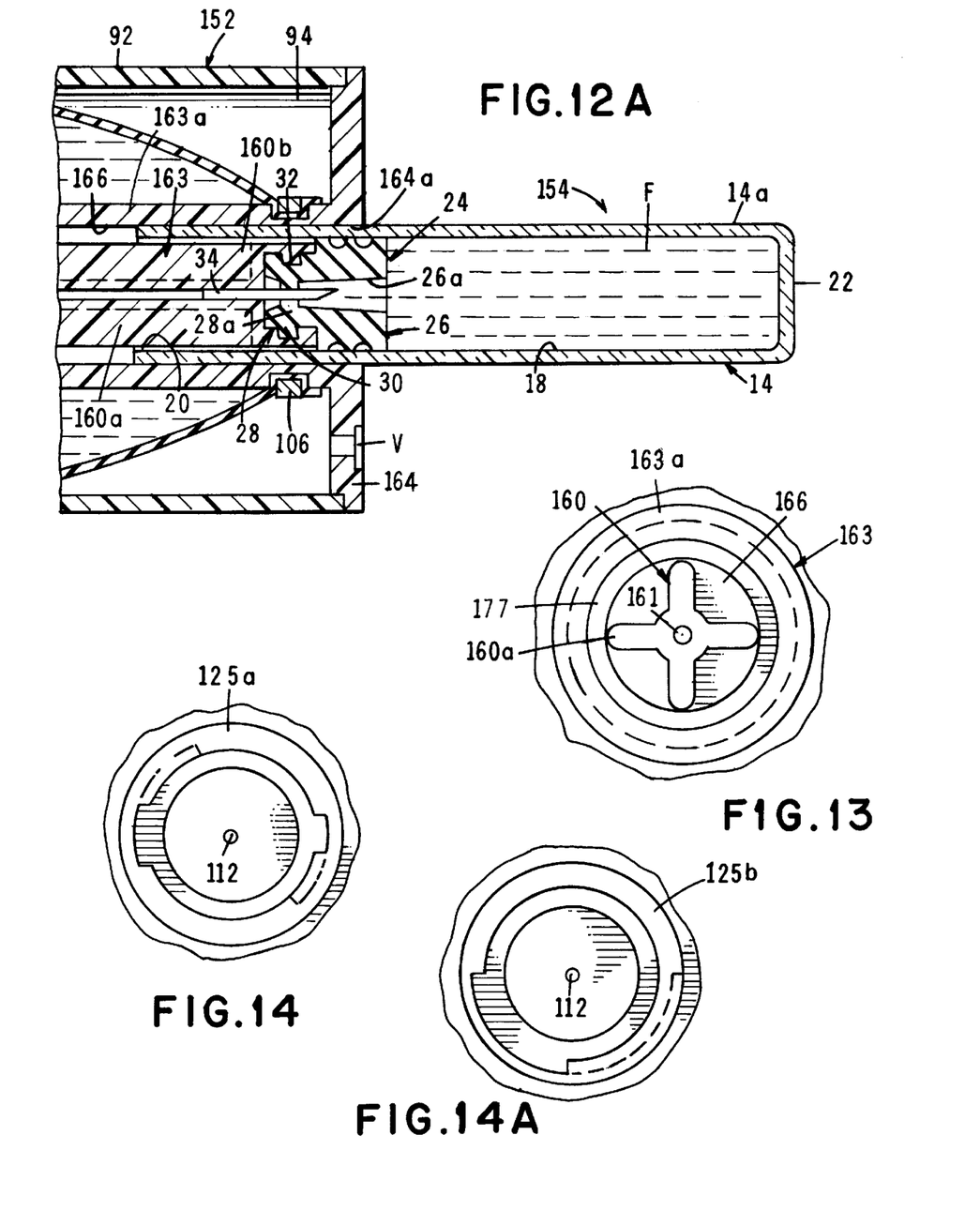
FIG. 13 is a cross-sectional view taken along lines 13—13 of FIG. 12.
FIG. 14 is an end view of an alternate form of the delivery component of the invention having a two slot rather than three slot hub-like configuration.
FIG. 14A is an end view of yet another form of the delivery component having a single slot hub-like configuration.

In a similar manner FIGS. 14 and 14A show alternate forms of hub-like portions there designated as 125a and 125b having tab-receiving slots of differing configuration. With this novel arrangement, fill assemblies containing a first medicament, such as morphine sulfate can be provided with a three-tab closure cap assembly 50 and the fluid delivery device can be provided with a mating three-slot, hub-like chamber defining portion 123. In like manner fill assemblies containing a second medicament, such as a first anti-infectant agent can be provided with a two-tab closure cap assembly 51a and the fluid delivery device can be provided with a mating two-slot, hub-like chamber defining portion 125a. When the fill assembly contains a third medicament such as an oncolytic agent, the fill assembly can be provided with a single-tab closure assembly 51b having a tab of a predetermined size and angular location. Similarly, the fluid delivery device can be provided with a single-slot, hub-like portion 125b in which the slot is specifically sized and located to receive the single locking tab of the closure cap. In this way, potentially serious errors of misadministration of medicaments can be elegantly and positively avoided.

After the peelable seals 130 and 130a (FIGS. 1 and 4) of adapter assembly 16 have been removed and after the container peelable seal 132 has been removed, the reservoir fill step can commence. This is accomplished by first mating the container assembly with adapter assembly 16. This done, the assemblage thus formed can be interconnected with the delivery component 90 in the manner previously described with the fill assembly mated with the delivery component. Fluid can be expelled from fluid chamber 18 of the container assembly into the fluid reservoir 100 of the dispenser component by urging container 14a into the annular space 136 defined by the interior wall of hollow housing 40 and the exterior surface of adapter body 46. This is accomplished by gripping finger engaging ears 138 (FIGS. 1 and 4) and then urging the container 14a inwardly with the thumb.

During the initial mating of container 14a with adapter subassembly 16, end 34a of cannula 34 will pierceably engage and penetrate wall 28a of connector 28 thereby opening fluid communication between reservoir 18 of container 14a and the internal fluid passageway 36 of cannula 34. Once wall 28a has been penetrated, an inward force exerted on container assembly 14 will cause body 46 to urge plunger 26 inwardly of container reservoir 18 from a first location proximate open end 20 to a second location proximate closed end 22. As plunger 26 moves inwardly, fluid within reservoir 18 will be caused to flow into central fluid passageway 36 of cannula 34 and toward inlet 112 of the support assembly 96. Fluid will then flow into fluid passageway 115 of assembly 96 and then into reservoir 100 via outlets 108. As the fluid under pressure flows through inlet passageways 108, the stored energy means, or elastomeric member 98 will be distended in the manner shown in FIG. 7 causing internal stresses to be built up within the elastomeric member, which stresses tend to return the member toward its less stressed initial starting state.

As previously discussed, prior use adapter assembly 16 is maintained in a protected and substantially sterile configuration by tear-away end caps 130 and 130a (see FIG. 1). As indicated in FIG. 1, tear-away end cap 130 is receivable over and closes the forward end of adapter assembly 16, while tear-away end cap 130a is received over and closes the rearward open end portion of the adapter assembly. Similarly, a barrier tear-away cap is emplaced over hub-like member 123 of the dispenser component to maintain that component in a closed and substantially sterile condition.

Once reservoir 100 has been filled, fluid will remain in the reservoir until a line clamp 140 of an infusion line 142 is opened (FIG. 7). Line 142 is connected proximate its inboard end to line connector 144 in the manner shown in FIG. 7. In addition to line 142, the infusion means on this form of the invention includes a gas vent and filter unit 146 which is disposed between line clamp 140 and connector 144. A suitable luer connector 147 is affixed to the outboard end of the infusion line. The infusion means also includes bolus injection means in the form of a conventional Y-site 148, for infusion into the patient a bolus dose of medication. After the line clamp is opened, the stored energy source of distendable membrane 98 will move from its second distended state toward its first relaxed state forcing fluid from reservoir 100 into delivery line 142 via outlets 110 and an outlet passageway 110a (FIG. 7).

Referring next to FIGS. 12 and 13, an alternate form of the fluid delivery apparatus of the present invention is there illustrated and generally designated by the numeral 150. This embodiment is similar in many respects to that shown in FIGS. 1 through 11 and like numbers are used in FIGS. 12 and 13 to designate like components. Once again the apparatus comprises a fluid delivery assembly 152 and a cooperating fill assembly 154.

The fill assembly of this latest form of the invention comprises a container subassembly 14 that is identical to that previously described and includes a body portion 14a, having a fluid chamber 18 for containing an injectable fluid "F". Body portion 14a is provided with a first open end 20, and a second closed end 22. First open end 20 is sealably closed by displacement means here provided in the form of a plunger assembly 24 made up of an elastomeric plunger 26 and a connector means, or connector 28 which functions to interconnect the container assembly with an adapter assembly which comprises a part of the reservoir fill assembly. Plunger assembly 24 is telescopically movable within chamber 18 of container subassembly 14 from a first location proximate first open end 20 to a second location proximate closed end 22.

As before, connector 28 includes threads 30 which can be threadably connected to threads provided on the pusher means of the adapter assembly 156 of this latest form of the invention. Connector 28 also includes a pierceable central wall 28a which is pierceable by one end of a cannula 34 that forms a part of adapter assembly 156. Cannula 34 comprises a part of the first flow control means of the adapter assembly for controlling fluid toward the fluid reservoir of the fluid delivery assembly 152. Connector 28 is integrally formed with plunger 26 so that as plunger 26 is moved toward closed end 22, connector 28 and plunger 26 will move as a unit.

In this latest form of the invention, adapter assembly 156 comprises a pusher member 160 which, in a manner presently to be described urges the displacement means longitudinally of chamber 18 of container 14a. Container subassembly 14 is telescopically receivable within open end of housing end plate 164 in the manner shown in FIG. 12 so that the housing can be moved from the first extended position shown in FIG. 2 to a second container encapsulation position wherein container 14 is substantially encapsulated within support assembly 163. Pusher member 160 includes an elongated, generally cross shaped pusher section 160a having an elongated fluid passageway 161 which communicates with cannula 34 and a head portion 160b to which connector 28 of the displacement means is threadably connected.

The fluid delivery assembly of this latest form of the invention comprises an elongated housing 92 having an internal chamber 94, a two-part support assembly 163 disposed within internal chamber 94, and extending longitudinally of the housing 92 and a generally cylindrically shaped, elongated elastomeric member 98. Elastomeric member 98, is identical to that previously described once again forms the stored energy means of the invention and is movable from a first relaxed state to a distended state. Member 98 cooperates with support assembly 163 to define a fluid reservoir 100, the outer boundary of which is defined by the distended elastomeric member 98.

Housing 92 comprises a cylindrically shaped central portion 92a and inlet and outlet end plates 164 and 165 respectively. Central section 92a and end plates 164 and 165 can be interconnected by any suitable rigid plastic material such as polycarbonate and the end plates can be affixed to the central portion by any suitable means such as adhesive bonding or an appropriate sonic weldment. Plate 164 of housing 92 has a first chamber 164a which receives support assembly 163 and also carries a vent means "V" for venting chamber 94. As before, elastomeric stored energy member 98 is securely affixed proximate its ends to support 163 by means of suitable ring clamps such as self-locking plastic pandit strips 106.

As shown in FIG. 12, support assembly 163 has cooperating first and second sections 163a and 163b. Section 163a is provided with an internal receiving chamber 166 within which pusher member 160 is disposed. Also disposed within chamber 166 is a second flow control means, the character of which is presently be described. Second section 163b of support assembly 163 is provided with fluid inlets 168 and fluid outlets 170.

The second flow control means of this latest form of the invention comprises valving means here provided as a conventional umbrella type first check valve 172 which is housed within chamber 166 formed in first support section 163a. More particularly, valve 172 is disposed within a subchamber 166a which is located proximate the inboard end of pusher member 160. Subchamber 166a is in communication with fluid passageway 161 and with inlet passageway 168. With this construction, first check valve 172 will permit fluid flow from passageway 161 toward inlet 168, but will block flow in the opposite direction.

To interconnect container assembly 14 with fluid delivery apparatus, the forward end of the container assembly is inserted into chamber 166 to bring connector 28 of the displacement means into engagement with the threaded extremity of pusher member 160. To threadably interconnect connector 28 with the pusher member, the container assembly is rotated. As the container assembly 14 is mated with pusher member 160, cannula 34 will pierce pierceable wall 28a of the displacement means thereby opening fluid communication between container chamber 18 and passageway 161 of the pusher member.

Fluid can be expelled from fluid chamber 18 of the container assembly into fluid passageway 161 by urging container 14a into the annular space 177 defined by the interior wall of section 163a and the exterior surface of pusher body 160. This will cause pusher body 160 to urge plunger 26 inwardly of container reservoir 18 from a first location proximate open end 20 to a second location proximate closed end 22. As plunger 26 moves inwardly, fluid within reservoir 18 will be caused to flow into the central fluid passageway cannula 34 and toward fluid passageway 161 of the pusher member. Fluid will then flow into subchamber 166a, past umbrella check valve 172 and then into reservoir 100 via outlets 168. As the fluid under pressure flows through inlet passageway 168, the stored energy means, or elastomeric member 98 will be distended in the manner shown in FIG. 12 causing internal stresses to be built up within the elastomeric member, which stresses tend to return the member toward its less stressed initial starting state.

Reservoir 100 can also be totally or partially filled by a secondary fill means shown here as a second check valve 180 which is housed within a second chamber 182 formed in end plate 165 of housing 92. Chamber 182 is in communication with inlets 168 formed in support section 163b via a central passageway 184 and is also in communication with fill port 186 formed proximate the outboard end of second chamber 182. Fill port 186 is normally closed by a closure cap 188 in the manner indicated in FIG. 12. With the construction shown, when cap 188 is removed and fill port is connected with a source of fluid under pressure, second check valve 180 will be moved inwardly into an open position so that the fluid can flow into reservoir 100. When the reservoir is filled, the check valve will return to its closed position.

Once clamp 191 of the infusion means of this latest form of the invention is opened, fluid will flow due to the urging of distended elastomeric membrane 98 into reservoir outlets 170 and into an annular passageway 198 formed in forward end cap 165. Disposed within passageway 198 is a rate control filter means here provided as a rate control filter sandwich 199 which functions to filter particulate matter from the fluid flowing from reservoir 100 and also functions to precisely control the rate of flow of fluid into the infusion line 193 of the infusion means. Sandwich 199 is of a conventional construction and is constructed from a thin circular shaped filter member 199a and a circular rate control member 199b of a predetermined porosity. In addition to clamp 191, bolus injection means, here shown as a conventional Y-site 197, is provided in line 193 to permit the injection of a bolus dose of medication to the patient.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A fluid delivery apparatus comprising
   (a) a fluid delivery assembly comprising:
      (i) a housing having a first chamber;
      (ii) a support assembly disposed within said housing and including:
         a. an elongated body having first and second communicating fluid passageways;
         b. a fluid inlet means for permitting fluid flow into said first fluid passageway formed in said elongated body portion; and
      (iii) stored energy means comprising an elongated tubular shaped elastomeric member circumscribing said elongated body and sealably connected proximate its ends to said elongated body, said elastomeric member having a central portion overlaying said second fluid passageway, said central portion of said elastomeric member being distendable by fluid flowing through said first and second fluid passageways from a first position in proximity with said elongated body to a second reservoir defining position where internal stresses are formed in said elastomeric member tending to return it to a less distended configuration;

(b) reservoir fill means interconnected with said fluid delivery assembly for filling said reservoir of said fluid delivery assembly, said reservoir fill means comprising:
      (i) a container assembly including a container having a fluid chamber and displacement means movable relative to said fluid chamber;
      (ii) an adapter assembly comprising a hollow housing having a barrel portion receivable within said first chamber of said housing of said fluid delivery assembly for connecting said adapter assembly to said fluid delivery assembly, said hollow housing having an outlet in communication with said fluid inlet means of said support assembly and a first open end for telescopically receiving at least a part of said container of said container subassembly and a second end; and
      (iii) pusher means for engagement with said displacement means of said container subassembly to move said displacement means relative to said fluid chamber of said container upon telescopic movement of said container to urge fluid from said outlet of said hollow housing.

2. The apparatus as defined in claim 1 in which said pusher means comprises a pusher member disposed within said hollow housing of said adapter assembly.

3. The apparatus defined in claim 1 in which said displacement means comprises a plunger member and a connector member, said connector member being interconnectable with said pusher means.

4. The apparatus as defined in claim 1 in which said housing includes a second chamber and in which said reservoir fill means further includes a check valve disposed within said second chamber for controlling fluid flow toward said stored energy means.

5. The apparatus as defined in claim 1 in which said fluid delivery assembly includes a septum and in which said adapter assembly includes an elongated cannula for piercing said septum.

6. The apparatus as defined in claim 1 in which said fluid delivery assembly includes a septum and in which said adapter assembly includes an elongated cannula having a fluid passageway, a first end for piercing said septum and a second end for piercing said displacement means.

7. The apparatus as defined in claim 6 further including vent means for venting to atmosphere gases contained within said fluid passageway of said elongated cannula.

8. The apparatus as defined in claim 7 in which said vent means comprises a hydrophobic vent element carried by said fluid delivery assembly.

9. A fluid delivery apparatus comprising:
   (a) a fluid delivery assembly comprising:
      (i) a housing having a chamber;
      (ii) a support assembly disposed within said housing, said support assembly comprising:
         a. an elongated body having first and second communicating fluid passageways; and
         b. a fluid inlet means for permitting fluid flow into said first fluid passageway formed in said elongated body portion; and
      (iii) stored energy means comprising an elongated tubular shaped elastomeric member circumscribing said elongated body and sealably connected proximate its ends to said elongated body, said elastomeric member having a central portion overlaying said second fluid passageway, said central portion of said elastomeric member being distendable to form a fluid delivery reservoir by fluid flowing through said first and second fluid passageways from a first position in proximity with said elongated body to a second reservoir defining position where internal stresses are formed in said elastomeric member tending to return it to a less distended configuration;

(b) fluid delivery reservoir fill means interconnected with said fluid delivery assembly for filling said fluid delivery reservoir, said reservoir fill means comprising:

(i) a container assembly including a container having a fluid chamber and displacement means movable relative to said fluid chamber;

(ii) an adapter assembly comprising a hollow housing having a barrel portion receivable within said chamber of said housing of said fluid delivery assembly for connecting said adapter assembly to said fluid delivery assembly, said hollow housing having an outlet in communication with said fluid inlet of said inlet means of said support assembly and a first open end for telescopically receiving at least a part of said container of said container subassembly and a second end;

(iii) pusher means for engagement with said displacement means of said container subassembly to move said displacement means relative to said fluid chamber of said container upon telescopic movement of said container to urge fluid to flow from said outlet of said hollow housing, said pusher means including an elongated hollow cannula having a fluid passageway; and (iv) vent means carried by said adapter assembly for venting to atmosphere gases contained within said fluid passageway of said hollow cannula.

10. The apparatus as defined in claim 9 in which said fluid delivery assembly includes a septum and in which said hollow cannula of said pusher means includes a first end for piercing said septum.

11. The apparatus as defined in claim 9 in which said fluid delivery assembly includes a septum and in which said hollow cannula of said pusher means has a first end for piercing said septum and a second end for piercing said displacement means.

12. The apparatus as defined in claim 9 in which said vent means comprises a hydrophobic vent element.

13. The apparatus as defined in claim 9 in which said pusher means comprises a pusher member disposed within said hollow housing of said adapter assembly.

14. The apparatus defined in claim 9 in which said displacement means comprises a plunger member and a connector member, said connector member being interconnectable with said pusher means.

15. The apparatus as defined in claim 9 further including infusion means for infusing fluid from said fluid delivery reservoir into a patient.

16. The apparatus as defined in claim 15 in which said infusion means comprises a delivery line connected to said fluid delivery assembly and communicating with said fluid delivery reservoir.

17. The apparatus as defined in claim 15 in which said infusion means further includes bolus injection means for infusion into the patient a bolus injection of medicament.

18. The apparatus as defined in claim 15 in which said barrel portion of said housing of said adapter assembly has at least one locking tab formed thereon and in which said chamber of said housing of said fluid delivery assembly is provided with at least one tab receiving slot for receiving said locking tab.

19. The apparatus as defined in claim 15 in which said barrel portion of said housing of said adapter assembly has a plurality of locking tabs formed thereon and in which said chamber of said housing of said fluid delivery assembly is provided with a plurality of tab receiving slots for receiving said plurality of locking tabs.

20. A fluid delivery apparatus comprising:

(a) a fluid delivery assembly for delivering fluids to a patient comprising:

(i) a housing having a chamber;

(ii) a support assembly disposed within said housing, said support assembly comprising:

a. an elongated body having first and second communicating fluid passageways; and b. a fluid inlet means for permitting fluid flow into said first fluid passageway formed in said elongated body portion; and (iii) stored energy means comprising an elongated tubular shaped elastomeric member circumscribing said elongated body and sealably connected proximate its ends to said elongated body, said elastomeric member having a central portion overlaying said second fluid passageway, said central portion of said elastomeric member being distendable to form a fluid delivery reservoir by fluid flowing through said first and second fluid passageways from a first position in proximity with said elongated body to a second reservoir defining position where internal stresses are formed in said elastomeric member tending to return it to a less distended configuration;

(b) fluid delivery reservoir fill means interconnected with said fluid delivery assembly for filling said fluid delivery reservoir, said reservoir fill means comprising:

(i) a container assembly including a container having a fluid chamber and displacement means movable relative to said fluid chamber;

(ii) pusher means including a fluid passageway in communication with said fluid inlet means of said support assembly for engagement with said displacement means of said container assembly to move said displacement means relative to said fluid chamber of said container to urge fluid to flow from said container into said fluid passageway of said pusher means; and (iii) vent means carried by said adapter assembly for venting to atmosphere gases contained within said chamber of said housing.

21. The apparatus defined in claim 20 in which said fluid delivery apparatus further includes infusion means connected to said fluid delivery assembly for infusion of fluids to the patient and in which said fluid delivery assembly further includes rate control means for controlling the rate of fluid flow from said reservoir toward said infusion means.

22. The apparatus as defined in claim 20 in which said support assembly further includes a first check for controlling fluid flow from said fluid passageway of said pusher means toward said stored energy means.

23. The apparatus as defined in claim 20 in which said pusher means is disposed within said support assembly.

24. The apparatus as defined in claim 20 in which said fluid delivery assembly further includes secondary fill means for filling said fluid delivery reservoir.

25. The apparatus as defined in claim 24 in which said fluid delivery assembly further includes infusion means for infusing fluid to the patient and also includes a second check valve for controlling fluid flow from said secondary fill means toward said fluid delivery reservoir.

26. The apparatus as defined in claim 25 in which said infusion means further includes bolus injection means for injection a bolus dose of medication to the patient.

27. The apparatus as defined in claim 26 in which said bolus injection means comprises a Y-site.

* * * * *